United States Patent
Jaeger et al.

[11] Patent Number: 4,999,303
[45] Date of Patent: Mar. 12, 1991

[54] MULTIPLATE SUBCULTURE SOLID MEDIA DEVICES

[75] Inventors: Thomas Jaeger, Wayne; Raymond T. Wasek, Jamesburg, both of N.J.

[73] Assignee: Becton, Dickinson and Company, Franklin Lakes, N.J.

[21] Appl. No.: 288,548

[22] Filed: Dec. 22, 1988

[51] Int. Cl.$^5$ ............... C12N 1/00; C12Q 1/00
[52] U.S. Cl. .................... 435/300; 435/33; 435/298; 435/299; 435/284; 435/296
[58] Field of Search .......... 435/30, 33, 34, 40, 435/298, 296, 299, 300, 301, 284; 215/214, 100 R

[56] References Cited

U.S. PATENT DOCUMENTS

| | | | |
|---|---|---|---|
| 3,589,983 | 6/1971 | Holderith et al. | 195/139 |
| 3,651,926 | 3/1972 | Elfast, Jr. | |
| 3,912,596 | 10/1975 | Haque et al. | 435/30 |
| 3,960,658 | 6/1976 | Avakian et al. | 435/33 |
| 4,308,347 | 12/1981 | Forrer et al. | 435/34 |
| 4,640,895 | 2/1987 | Davis | 435/300 |

FOREIGN PATENT DOCUMENTS 111664A 10/1982 European Pat. Off.

Primary Examiner—Robert A. Wax
Assistant Examiner—William Chan
Attorney, Agent, or Firm—Robert P. Grindle

[57] ABSTRACT

A multiplate subculture solid media device is provided with a connection for internal flow communication with a liquid medium culture bottle. The device includes a large transparent screw cap on one face thereof to gain easy access to the plurality of media plates for direct examination and sample taking through the growth period. However, the cap is transparent and of a size allowing continuous examination during the growth period without any opening. As a further feature of the invention, the screw cap may include an integral magnifying lens for enhancing the continuous examination of culture growth.

8 Claims, 1 Drawing Sheet

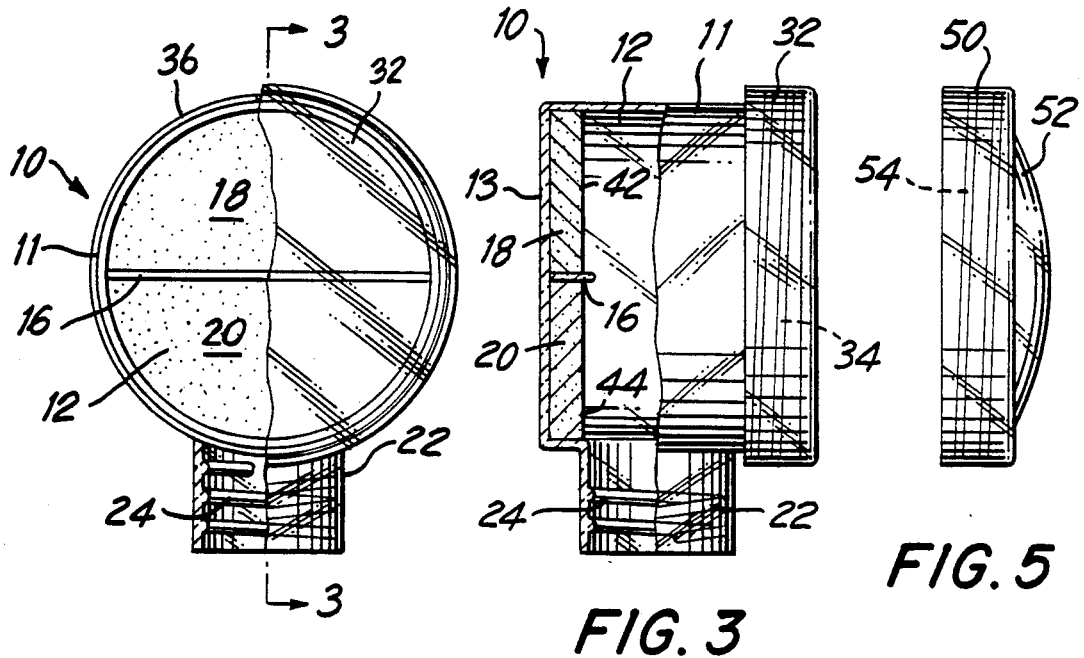

MULTIPLATE SUBCULTURE SOLID MEDIA DEVICES

BACKGROUND AND STATEMENT OF THE INVENTION

This invention relates to a device for the detection of microorganisms in a body fluid sample. More particularly, this invention relates to a device containing at least one solid medium in combination with a connection for the device to a liquid medium culture bottle or container. The device provides for proper exposure of the two media (solid and liquid) to the sample under investigation while at the same time providing complete noncovered access to the solid media during the growth period for taking samples or close examination.

With the device of the invention, once the microorganisms begin growth, they may be examined directly without any glass or plastic covering interfering with the examination. Alternatively, they may be examined in their entirety through the transparent covering forming the access entry to the device of the invention.

In the detection of microorganisms in body fluids, particularly bacteria in blood, there is a requirement that a sample of the fluid be used to inoculate a liquid nutrient medium. Subsequent to this, the liquid medium is, after incubation, in turn, used to inoculate one or more solid media to obtain colony growth of the organisms. Generally, devices have been provided in which both the liquid and the solid culture media are combined in the same container. This overcomes any problems involving exposure during transfer of these cultures in the liquid medium to the solid culture medium in another container. Representative of such devices is that described in U.S. Pat. No. 3,589,983, issued June 29, 1981. Other patents directed to the subject matter of the invention include U.S. Pat. No. 3,651,926, issued Mar. 28, 1972; U.S. Pat. No. 4,308,347, issued Dec. 29, 1981; and U.S. Pat. No. 4,678,753, issued July 7, 1987.

There are problems, however, with combined devices in that the constituents of the solid medium may be dissolved in the liquid medium. Thus, only solid media compatible with the liquid medium can be utilized. If the solid media constituents pass into the liquid medium, differentiations of the pathogens may no longer be possible.

With the present invention, the solid medium and the liquid medium are appropriately separated, but may be connected together in order to provide the proper exposure of the solid medium, or media, to the liquid medium containing the sample under consideration. Nevertheless, once the colony growth period has taken place, the device of the invention may be disassembled to the extent whereby the solid media plates may be examined completely and directly without any interference from a covering therefor. Alternatively, with the invention here, a magnifying cover is provided as an alternative for a close examination without direct access or exposure to the solid media under consideration.

That is, the device of the invention includes a main structure supporting one or more solid media. This structure includes a connection for connecting the main or base structure to a liquid culture medium container. The main base structure carrying the solid media may be generally cylindrical with one solid wall for supporting the solid medium and the opposite wall thereof being in the form of a transparent screw cap with a liquid tight connection so that once the sample has been introduced into the liquid medium container, the device of the invention may be connected thereto and the solid medium may be exposed to the liquid medium containing the sample of interest.

The exposure is only intermittent, as required and desired, in order to provide the appropriate culture development during the incubation or colony growth period of the inoculated solid media present in the device of the invention. Because of the large cap which is transparent, the growth character may be examined throughout the incubation period either by the examination indirectly through the transparent cap, or by removal of the cap for direct examination and sampling of the various media plates supported on the device of the invention. Once the incubation period has taken place, the cap of the device may be removed so that the entire solid media with the cultured organisms present thereon may be exposed for examination by the laboratory technician.

Again, during the examination period, if the embodiment utilizing the magnifying lens on the cap of the invention is used, the character of the growth during the incubation period may be carefully examined without any opening of the container containing the solid medium. In this way, exposure to contamination is reduced, as will be understood. Moreover, there is less likely to be an inadvertent contamination of the specimen under consideration with the arrangement herein.

Other objects and advantages of the invention will be apparent from the following description, the accompanying drawings, and the appended claims.

DESCRIPTION OF THE DRAWINGS

FIG. 1 is an elevational view, partly in section, of a device illustrating the invention;

FIG. 2 is a perspective view of a liquid medium container representative of the type to which the device of the invention is attached for culturing;

FIG. 3 is a cross sectional view taken along lines 3—3 of FIG. 1;

FIG. 4 is a sectional view similar to FIG. 3 but with the cap of the invention removed;

FIG. 5 is a side elevational view of one embodiment of the cap of the invention showing the integral magnifying lens thereof; and FIG. 6 is a view of an embodiment of the invention similar to that shown in FIG. 1, but illustrating the partitioning of the support structure of the invention for a large number of solid media plates.

DETAILED DESCRIPTION OF THE INVENTION

Referring to the drawings in which like reference characters refer to like parts throughout the several views thereof, in FIG. 1, the reference numeral 10 designates the device of the invention having a cylindrical body 11 defining a chamber 12. As can be seen in FIGS. 1 and 3, chamber 12 includes a back wall 13 supporting two solid media plates 18, 20 divided by a divider arrangement 16. As can be seen further in FIGS. 1 and 3, a cap 32 is screwed on the right-hand face of cylindrical body 11, as shown in FIG. 3 with the cooperating threads 34 of transparent cap 32 cooperating with the threads 36 formed on the right hand face 40 of body 11, as shown in FIG. 4, for example.

The cylindrical body 11 includes an integral neck or extension 22 having internal threads 24 for cooperating with threads 30 on the neck 28 of a liquid culture media bottle 26 as shown in FIG. 2. Thus, as can be seen in FIGS. 3 and 4, the solid media surface 42, 44 of plates 18, 20 may be exposed to a liquid culture medium once the cylindrical body 11 is screwed upon a liquid culture medium container 26 shown in FIG. 2.

When this takes place, and assuming a cap such as 32 has been screwed upon the opposing open front face 40 of the device 10, the entire combined arrangement may be inverted in order to provide liquid culture flow into the chamber 12 of the cylindrical body 11 whereupon the surfaces 42, 44 are exposed to the liquid medium for a period of time required prior to removal of the liquid media so that cell growth may commence on surfaces 42, 44. It will be understood that each of the threaded connections 24, 30 and 34, 36, for example, may incorporate sealing washers, not shown for clarity, in order to enhance the seal against any leakage of culture media.

During this period of cell growth, because of the transparent nature of the cap 32 and its large size, the surfaces 42, 44 are clearly visible through the transparent cap 32 so that the nature and condition of the growth during the incubation period can be examined. Alternatively, the laboratory technician may remove cap 32 for a direct examination and sampling. Because of the enlarged front end opening of the device 10, the surfaces of the solid plates on the opposite wall of chamber 12 are readily accessible for examination.

In this connection, reference is made to FIG. 5 where an alternative embodiment 50 of cap 32 is shown. This embodiment includes a transparent integral lens 52. Thus, cap 50 with internal screw threads 54 may cooperate with threads 36 as shown in FIG. 4 on front end 40 of the unit 10 so that the alternative embodiment cap 50 may be screwed upon the front end of the device. Thus, the technician has the additional advantage of magnification of the condition of the growth during the period of time when examination is required. The laboratory technician need not, therefore, with this embodiment, open the container as frequently (or at all) because detailed examination takes place with the magnification of cap 50.

Referring now to FIG. 6, a further embodiment of cylindrical container device 60 of the invention is shown. This embodiment illustrates a larger number of solid media plates which may be formed. Thus, plates 64 and 66 may take up one quarter of the rear wall of the device 60 being divided by a divider arrangement 76. Alternatively, smaller media areas 70 and 72 may be formed to provide one-eighth of the surface for two different solid media contents with a divider 78. As stated above, with either form of the embodiment shown above, the device thus formed is then tilted several times to guarantee to optimum contact between the liquid and the solid nutrient media. The apparatus may then be incubated at a temperature of, for example, within the range of between about 20° C. and 37° C. for from one hour up to perhaps, ten days after which the growth present on the media is observed and evaluated. As stated above, further, because of the magnifying feature of one embodiment, this evaluation can take place without any actual entry into the container chamber 12.

Alternatively, either the cap 32 embodiment or the cap 50 embodiment may be unscrewed for providing a full wall opening for access to the solid media plates on the opposite wall. Thus, the technician may take samples, if required, for further examination outside the device. However, during the period of incubation, if no growth can be detected, the incubation period process can be repeated several times without any opening because an examination will clearly show with the device of the invention that no growth has taken place. In cases of long incubations, for example, the device may be tipped at least once a day to guarantee optimum contact between the liquid media in the culture bottle 26, and the solid media plates of the invention.

Thus, as will be appreciated from the above description, there is provided in accordance with this invention, a device for culturing organisms wherein both solid and liquid culture media are required, with the device being particularly appropriate for examination of organisms during the incubation period of the device. That is, the device provides the complete alternatives of direct access or simply a thorough indirect examination.

Moreover, the assembly is comprised of multiple parts of thermoplastic materials which may be mass produced, as will be understood, from a variety of materials, including, for example, polyethylene, polypropylene and polycarbonate. Also, preferably the entire device is transparent to simplify observation.

While the forms of apparatus herein described constitute preferred embodiments of the invention, it is to be understood that the invention is not limited to these precise forms of apparatus and that changes may be made therein without departing from the scope of the invention which is defined in the appended claims. For example, whereas one form of arrangement is shown wherein the device of the invention is in tubular form, it is to be understood that the basic unit of the invention may be square with a circular front face for incorporating integral screw threads for receiving the cap of the invention. The limitation is only that the device cap be transparent for ready observation of the solid media for the development of organisms thereon during the incubation period so that the user will know when the cap may be removed for complete direct observation of the developed organisms.

What is claimed is:

1. A device for culturing microorganisms wherein a sample of interest is to be exposed to both a solid and a liquid culture medium, characterized by
   (a) an elongated body defining a solid growth medium chamber;
   (b) a solid wall forming one end of said elongated body;
   (c) a plurality of solid medium plates positioned on said solid wall;
   (d) an opening forming the end of said elongated body opposite said solid wall;
   (e) a transparent cap for said open end;
   (f) cooperating connecting means on said open end of said elongated body and said transparent cap for holding said cap in sealing engagement with said open end of said elongated body;
   (g) an extension extending integrally from said elongated body between said solid wall and said open end thereof;
   (h) a bore extending through said extension and in flow communication with said chamber; and
   (i) internal screw threads in said bore.

2. The device of claim 1, further characterized by
   (a) said cooperating connecting means are external screw threads on said open end of said elongated body and internal screw threads on said cap.

3. The device of claim 1, further characterized by
(a) said cap includes an integral magnifying element.
4. The device of claim 1, further characterized by
(a) said elongated body is cylindrical.
5. An assembly for culturing microorganisms, characterized by
(a) a liquid culture medium bottle;
(b) said bottle having a closed end and an open end;
(c) a neck on said bottle adjacent the open end;
(d) external threads on said neck; and
(e) a device for connection to said external threads, said device comprising
  (1) an elongated body defining a solid growth medium chamber;
  (2) a solid wall forming one end of said elongated body;
  (3) a plurality of solid medium plates positioned on said solid wall;
  (4) a opening forming the end of said elongated body opposite said solid wall;
  (5) a transparent cap for said open end;
  (6) cooperating connecting means on said open end of said elongated body and said transparent cap for holding said cap in sealing engagement with said open end of said elongated body;
  (7) an extension extending integrally from said elongated body between said solid wall and said open end thereof;
  (8) a bore extending through said extension and in flow communication with said chamber;
  (9) internal screw threads in said extension for connection to the external threads on the said neck of said liquid culture bottle.
6. The device of claim 5, further characterized by
(a) said cooperating connecting means are external screw threads on said open end of said elongated body and internal screw threads on said cap.
7. The device of claim 5, further characterized by
(a) said cap includes an integral magnifying element.
8. The device of claim 5, further characterized by
(a) said elongated body is cylindrical.

* * * * *